United States Patent [19]

Kaneko

[11] Patent Number: 5,429,996
[45] Date of Patent: Jul. 4, 1995

[54] BONE GRAFTING MATERIAL

[75] Inventor: Norio Kaneko, Yokohama, Japan

[73] Assignee: Nikon Corporation, Tokyo, Japan

[21] Appl. No.: 131,524

[22] Filed: Sep. 22, 1993

[30] Foreign Application Priority Data

Oct. 9, 1992 [JP] Japan .................................. 4-271280

[51] Int. Cl.⁶ ............................................. C03C 13/06
[52] U.S. Cl. ........................................ 501/35; 501/58;
501/63; 501/65; 501/72; 106/35; 433/217.1;
433/201.1; 623/11; 623/16
[58] Field of Search ........................ 501/35, 36, 58, 63,
501/65, 72, 32; 106/35; 433/217.1, 229, 201.1;
633/11, 16, 18

[56] References Cited

U.S. PATENT DOCUMENTS

| | | | |
|---|---|---|---|
| 3,981,736 | 9/1976 | Broemer et al. | 501/63 |
| 4,131,597 | 12/1978 | Blüethgen et al. | 260/42.18 |
| 4,171,544 | 10/1979 | Hench et al. | 106/676 |
| 4,239,113 | 12/1980 | Gross et al. | 206/568 |
| 4,604,097 | 8/1986 | Graves, Jr. et al. | 623/11 |
| 4,608,350 | 8/1986 | Howard, Jr. | 501/58 |
| 4,613,577 | 9/1986 | Tagai et al. | 501/35 |
| 4,735,857 | 4/1988 | Tagai et al. | 428/388 |
| 4,820,573 | 4/1989 | Tagai et al. | 428/228 |
| 4,851,046 | 7/1989 | Low et al. | 106/35 |
| 5,108,957 | 4/1992 | Cohen et al. | 501/63 |
| 5,120,340 | 6/1992 | Ducheyne et al. | 65/18.3 |

FOREIGN PATENT DOCUMENTS

| | | |
|---|---|---|
| 0206726 | 12/1986 | European Pat. Off. . |
| 2393020 | 12/1978 | France . |
| 2548658 | 1/1985 | France . |
| 63-14989 | 4/1988 | Japan . |
| WO8604807 | 8/1986 | WIPO . |

Primary Examiner—Deborah Jones
Attorney, Agent, or Firm—Shapiro and Shapiro

[57] ABSTRACT

A bone grafting material for use in medicine is glass wool which has the mean diameter of 100 μm or less and whose composition is:

$SiO_2$ 40–62% (w/w)
$Na_2O$ 10–32% (w/w)
$CaO$ 10–32% (w/w)
$P_2O_5$ 0–12% (w/w)
$CaF_2$ 0–12% (w/w)
$B_2O_3$ 0–20% (w/w),

When the grafting material is used for treatment of periodontal disease, the grafting material is completely replaced by newly formed bone, whereby dental ankylosis of the grafting material to a tooth root does not occur and the newly formed bone and the tooth root are bound with a tissue like a periodontal membrane.

1 Claim, No Drawings

BONE GRAFTING MATERIAL

BACKGROUND OF THE INVENTION

1. Field of the Invention

The present invention relates to a bone grafting material for use in medicine.

1. Related Background Art

Ceramics such as hydroxyapatite and tricalcium phosphate (TCP) as well as crystallized glass such as A-W ceramics have osteoconduction, and granular, porous and block materials are clinically applied as bone grafting materials for treatment of bone defect.

The grafting materials, which are artificial, are foreign bodies to an organism. And preferably, these materials are completely replaced by newly formed bone after the bone restoration treatment. In the treatment of periodontal disease, it is desirable to avoid dental ankylosis of the grafting materials to the tooth root. It is also desirable that newly formed bone and the tooth root be bound with a periodontal-membrane-like tissue and cementum.

While having capacity to regenerate bone, the above-mentioned conventional grafting materials are taken in to remain in the newly formed bone, which causes undesirable dental ankylosis. Granular grafting materials may come out of the gap between gingiva and tooth root, which hinders sufficient restorative effect. Also it is extremely difficult to fiberize bioactive ceramics and glass ceramics.

SUMMARY OF THE INVENTION

The object of the present invention is to solve the above-mentioned problems.

In order to achieve this object, the present invention provides a bone grafting material for use in medicine which is glass wool having a mean diameter of 100 $\mu$m or less and whose composition is:

$SiO_2$ 40–62% (w/w)
$Na_2O$ 10–32% (w/w)
$CaO$ 10–32% (w/w)
$P_2O_5$ 0–12% (w/w)
$CaF_2$ 0–12% (w/w)
$B_2O_3$ 0–20% (w/w).

When used in treatment of periodontal disease, the bone grafting material of the present invention is completely replaced by the newly formed bone after bone restoration treatment, whereby dental ankylosis of the grafting material to the tooth root does not occur and the newly formed bone and the tooth root are bound with the periodontal-membrane-like tissue.

The process in which the present invention produces such bone restorative effect is not yet known. However, it is probable that the above-mentioned effect is produced by the osteoconduction of the bioactive glass grafting material, the stimulation given to the organism by the ions of the components of the grafting material which flow out in vivo as well as the dissolution of the glass wool grafting material which occurs in vivo during the bone restoration treatment.

The rate of dissolution of the glass wool can be controlled by changing the diameter of the short fibers or composition of the glass. Thus, the glass wool can be prepared according to the application thereof. In addition, the outflow of the grafting glass from the position into which it is tilled can be prevented by forming the glass as short fibers so that the effect of the bioactive glass may be fully exerted.

The glass according to the present invention may consist of $SiO_2/Na_2O/CaO/P_2O_5/CaF_2/B_2O_3$, more preferably, of $SiO_2/Na_2O/CaO/P_2O_5$.

$Na_2O$ may be replaced by another alkaline metal oxide (for example, $K_2O$, $Li_2O$, and so on). Part of CaO may be replaced by another alkaline earth metal oxide (for example, MgO). Further, oxides other than the essential components $SiO_2$, $Na_2O$ and CaO (for example, $ZrO_2$, $TiO_2$, $La_2O_3$, $Al_2O_3$, $Ta_2O_5$ $Nb_2O_5$, and so on) and fluorides (for example, NaF, $Na_2SiF_6$) may be added.

If the diameter of the short fibers of the glass wool is too large, the grafting material becomes brittle and cannot be tilled properly. On the other hand, if the diameter is too small, the grafting material is dissolved in vivo before being replaced by the newly formed bone and proper bone restoration is not carried out. Accordingly, the mean diameter of the short fibers is preferably 1–100 $\mu$m, more preferably 2–50 $\mu$m, and most preferably 5–20 $\mu$m.

The effect of the bone grafting material of the present invention was verified by experiment of treatment of periodontal disease, but this bone grafting material can be applied to other bone restoration treatment. It can be filled in the gap between an artificial tooth and a bone in order to graft the artificial tooth root to the bone, and can be used for treatment of resorption of cervical bone in order to regenerate bone around an artificial tooth root. In addition, this grafting material can be used in combination with the GTR method. Thus, further effects can be expected.

The grafting material of the present invention may be prepared by the vapor spray process, the spinning process, the flame attenuation process, the rotary process, and so on. The process of preparing the grafting material of the present invention is not limited to those mentioned.

Now a specific embodiment of the present invention will be described. The embodiment is merely illustrative and does not set any limit to the present invention.

DETAILED DESCRIPTION OF THE PREFERRED EMBODIMENT

Glass wool of bioactive glass having a composition of $SiO_2$ (46.1% (w/w))/$Na_2O$ (24.4% (w/w))/CaO (26.9% (w/w))/$P_2O_5$ (2.6% (w/w)) were prepared so as to have the mean diameter of 2–50 $\mu$m.

The glass wool was filled in a periodontal diseased region (i.e. defect in jaw bone around a tooth) which had been experimentally formed in the jaw bone of an adult dogs. After four months, condition of the diseased part was determined by examining pathological specimens. The result showed that the glass wool had been completely replaced by newly formed bone, that dental ankylosis of the grafting material to the tooth root had not been formed, and that the newly formed bone and the tooth root had been bound with a periodontal-membrane-like tissue.

As described above, when the bone grafting material of the present invention is used for treatment of periodontal disease, the grafting material is completely replaced by newly formed bone after bone restoration treatment, whereby dental ankylosis of the grafting material to the tooth root does not occur and the newly formed bone and the tooth root are bound with the periodontal-membrane-like tissue.

What is claimed is:

1. A bone grafting material for use in medicine which is glass wool having a mean diameter of 100 μm or less and the following composition:

$SiO_2$ 40–62% (w/w)
$Na_2O$ 10–32% (w/w)
$CaO$ 10–32% (w/w)
$P_2O_5$ 0–12% (w/w)
$CaF_2$ 0–12% (w/w)
$B_2O_3$ 0–20% (w/w).

* * * * *